(12) United States Patent
Martin

(10) Patent No.: US 9,657,042 B2
(45) Date of Patent: May 23, 2017

(54) SILANE COMPOUNDS AND USE OF SAME FOR FUNCTIONALIZING SOLID SUPPORTS AND IMMOBILIZING BIOLOGICAL MOLECULES ON THESE SUPPORTS

(75) Inventor: Franck Martin, Montpellier (FR)

(73) Assignee: COMMISSARIAT A L'ENERGIE ATOMIQUE, Paris (FR)

( * ) Notice: Subject to any disclaimer, the term of this patent is extended or adjusted under 35 U.S.C. 154(b) by 1599 days.

(21) Appl. No.: 12/162,793

(22) PCT Filed: Feb. 1, 2007

(86) PCT No.: PCT/EP2007/050984
§ 371 (c)(1),
(2), (4) Date: Aug. 12, 2008

(87) PCT Pub. No.: WO2007/088187
PCT Pub. Date: Aug. 9, 2007

(65) Prior Publication Data
US 2009/0029875 A1   Jan. 29, 2009

(30) Foreign Application Priority Data

Feb. 1, 2006 (FR) .................... 06 50361

(51) Int. Cl.
| C07F 7/02 | (2006.01) |
| C07F 9/40 | (2006.01) |
| C07F 7/08 | (2006.01) |
| C07F 7/12 | (2006.01) |
| C07F 7/18 | (2006.01) |

(52) U.S. Cl.
CPC .......... *C07F 9/4053* (2013.01); *C07F 7/0896* (2013.01); *C07F 7/12* (2013.01); *C07F 7/1836* (2013.01); *C07F 9/409* (2013.01); *C07B 2200/11* (2013.01)

(58) Field of Classification Search
None
See application file for complete search history.

(56) References Cited

U.S. PATENT DOCUMENTS

| 3,122,518 | A |   | 2/1964 | Logemann et al. |
| 4,338,454 | A | * | 7/1982 | Wesson et al. ............... 556/445 |
| 4,339,581 | A | * | 7/1982 | Totten ................... A01N 55/00 546/14 |
| 5,277,813 | A | * | 1/1994 | Feibush et al. ............ 210/502.1 |
| 2004/0039116 | A1 |   | 2/2004 | Vinet et al. |
| 2005/0277155 | A1 |   | 12/2005 | Vinet et al. |

FOREIGN PATENT DOCUMENTS

| EP | 1 683 571 |   | 7/2006 |
| JP | 63051393 |   | 3/1988 |
| JP | 3-68588 | * | 3/1991 |
| JP | 200570369 | * | 3/2005 |
| JP | 2005070369 |   | 3/2005 |
| WO | WO 02/051856 |   | 7/2002 |
| WO | WO 2005/027240 |   | 3/2005 |

OTHER PUBLICATIONS

Gershevitz et al (2003 JACS 125:4730-4731).*
Gimpel et al (1982 Chromatographia 16:117-125).*
International Search Report, completed Apr. 4, 2007, in International Patent Application No. PCT/EP2007/050984, filed Feb. 1, 2007.
French Search Report, dated Sep. 8, 2006, in corresponding French Patent Application. No. 0650361, Feb. 1, 2006.

* cited by examiner

*Primary Examiner* — Christopher M Gross
(74) *Attorney, Agent, or Firm* — Brinks Gilson & Lione

(57) ABSTRACT

The invention relates to novel silane compounds corresponding to the formula (I) below:

$$A\text{-}E\text{-}X \qquad (I)$$

in which:
X represents a silyl group capable of creating a covalent bond after reaction with the hydroxyl or hydride functional groups of a support;
E represents an organic spacer group;
A represents a group chosen from the groups of formulae below:

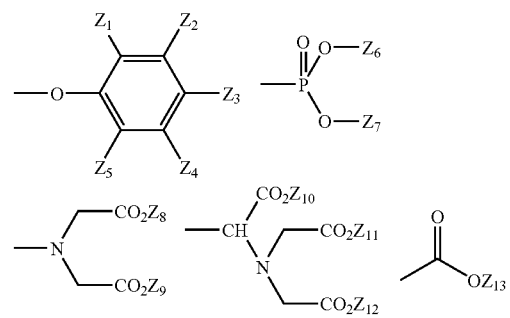

in which:
$Z_1$ to $Z_5$ independently represent a hydrogen atom or a halogen atom;
$Z_6$ and $Z_7$ represent a group for protecting the phosphonic acid functional group, a hydrogen atom or a monovalent cation;
$Z_8$ to $Z_{12}$ independently represent a group for protecting the carboxylic acid functional group, a hydrogen atom or a monovalent cation; and
$Z_{13}$ represents an imidazole, N-hydroxysuccinimide, nitrophenyl, pentafluorophenyl or acid anhydride group.

Use of these silane compounds for functionalizing solid supports and for immobilizing biological molecules on these supports.

1 Claim, No Drawings

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 1
tttttgataa acccc                                                    15

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
catagagtgg gtttatcca                                                19

SILANE COMPOUNDS AND USE OF SAME FOR FUNCTIONALIZING SOLID SUPPORTS AND IMMOBILIZING BIOLOGICAL MOLECULES ON THESE SUPPORTS

This application is a National Stage application of International Application No. PCT/EP2007/050984 filed Feb. 1, 2007, the entire contents of which are hereby incorporated herein by reference. This application also claims the benefit under 35 U.S.C. §119 of French Patent Application No. 0650361 filed Feb. 1, 2006, the entire contents of which are hereby incorporated herein by reference.

TECHNICAL FIELD

The present invention relates to novel silane compounds that can be used for functionalizing solid supports, to supports functionalized by said silane compounds and to their uses for the immobilization of biological molecules, such as nucleic acids, polypeptides, lipids, carbohydrates and hormones.

Supports bearing immobilized biological molecules are advantageously used for the detection and recognition of biological species, but also for other applications, such as the separation and purification of biological molecules.

In order to do this, it is essential to have functionalized solid supports that exhibit the following characteristics:
- enable the reproducible immobilization of the biological molecules of interest;
- enable the immobilization of the biological molecules of interest in a substantial manner, the sensitivity of a functionalized solid support depending on the degree of immobilization and on the method of detecting a signal but also on the level of background noise;
- be reusable.

The immobilization of biological molecules of interest on solid supports is generally carried out in two steps:
- a first step of functionalizing the supports which consists of a chemical modification of their surface by grafting of coupling agents which will ensure the attachment of the biological molecules to the support; and
- a second step of immobilization consisting in establishing an interaction between the biological molecules and the coupling agents grafted to the support, the interaction possibly consisting of the formation of a covalent bond between the biological molecule and the coupling agent or of weaker bonds (such as electrostatic interactions, or dipolar bonds).

The coupling agents are grafted to the surface of the supports via reaction with the —OH or hydride functional groups of the support and the reactive functional groups of the agent, in order to form strong ionic or covalent interactions between the coupling agent and the support and are arranged at the surface of the support generally in the form of a dense monolayer that is organized at the surface, for example by formation of van der Waals type bonds between the grafted coupling agent molecules.

Coupling agents for functionalizing the supports, in particular silicon-based supports, are organosilanes, comprising at least one organic group R capable of reacting with a functional end of the molecules to be immobilized and at least one group X capable of reacting with the —OH or hydride functional groups of the support to form an ionocovalent or even covalent bond.

The inventors set themselves the objective of providing novel silane compounds capable of being grafted to the surface of a solid support and comprising groups that enable the immobilization of biological molecules, either by formation of covalent bonds, or by formation of interactions of lower energy than the covalent bond (electrostatic interactions, complexation, etc.).

SUMMARY OF THE INVENTION

Thus, the invention relates, according to a first subject matter, to a silane compound corresponding to one of the following formulae:

$$A\text{-}E\text{-}X \quad (I)$$

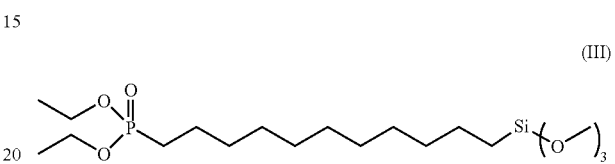

(III)

A, E and X in the formula (I) corresponding to the following definitions:
- X represents a silyl group capable of creating a covalent bond after reaction with the hydroxyl or hydride functional groups of a support;
- E represents an organic spacer group; and
- A represents a group chosen from the groups of formulae below:

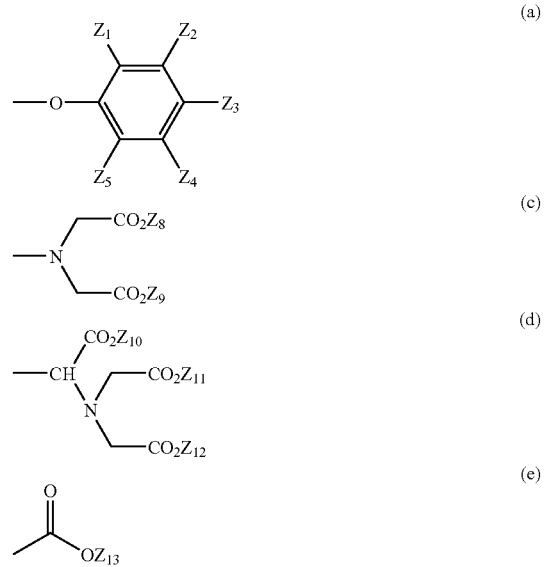

in which:

$Z_1$ to $Z_5$ independently represent a hydrogen atom or a halogen atom;

$Z_8$ to $Z_{12}$ independently represent a group for protecting the carboxylic acid functional group, a hydrogen atom or a monovalent cation; and $Z_{13}$ represents an imidazole, N-hydroxysuccinimide, nitrophenyl, pentafluorophenyl or acid anhydride group, with the exclusion of phenyloxyundecyltrimethoxysilane and compounds of the following formulae:

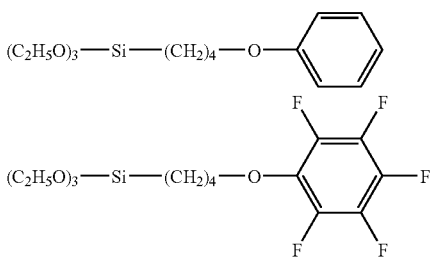

According to the invention, the E group is an organic spacer group, its main function being to confer particular properties on the film resulting from the grafting of silane compounds to the surface of a support.

This E group is generally a hydrocarbon-based group, for example comprising from 2 to 24 carbon atoms, and optionally comprising one or more unsaturations and/or one or more aromatic groups and/or one or more heteroatoms.

By way of example, the E group may be an alkylene group, that is to say a chain of the —CH$_2$— type, for example comprising from 8 to 24 carbon atoms. This type of group gives the silane compounds, once grafted to a support, an ability to interact together, by creation of interchain interactions and thus contributes to obtaining organized monolayers.

The E group may be a fluoroalkylene group comprising from 3 to 24 carbon atoms. These groups help to give the film resulting from the grafting of the silane compounds comprising them, properties that enable them to be used in chromatography and in electrophoresis.

The E group may be a hydrocarbon-based group comprising one or more unsaturations, for example of the acetylene type. An example of such a group may be an alkylene group as defined above interrupted by one or more acetylene unsaturations. When the E group comprises at least two unsaturations, it may give the silane compounds, once grafted to a support, an ability to be crosslinked.

The E group may also be a hydrocarbon-based group comprising one or more aromatic groups.

Mention may be made, for example, of a group comprising aromatic groups conjugated with linear unsaturated groups, such as a group resulting from the linking of a phenylene-vinylene or phenylene-acetylene unit. These groups help to give the film that results from the grafting of the silane compounds comprising them, non-linear optical properties.

Mention may be made, for example, of a group comprising pyrrole or thiophene units. These groups help to give the film that results from the grafting of the silane compounds comprising them, electron conduction properties.

Mention may be made, for example, of a group comprising one or more aromatic groups substituted by one or more heteroatom groups, such as a group comprising a chain of quinone units or of diazo units. These groups help to give the film that results from the grafting of the silane compounds comprising them, photoluminescence/electroluminescence properties.

According to the invention, X represents a silyl group enabling the covalent attachment of the silyl compound to the hydroxyl or hydride functional groups of a support, said support may be, for example, a solid support made of silicon, made of ITO (indium tin oxide) or made of titanium.

This X group may be, for example, a trihalosilane group (such as a trifluorosilane, or trichlorosilane group); a trihydrosilane group; a trialkoxysilane group —Si(OR)$_3$ with R representing a linear or branched $C_1$ to $C_6$ saturated alkyl group or a phenyl group (such as a trimethoxysilane group, a triethoxysiloxane group or a triisopropoxysilane group); a triaminoalkoxyamine group —Si(NR$^1$R$^2$)$_3$, with R$^1$ and R$^2$ independently representing a linear or branched $C_1$ to $C_6$ saturated alkyl group or a phenyl group; or an organometallic group (such as an organomagnesium group or an organolithium group); or a hydrolysable group.

The $Z_8$ to $Z_{12}$ groups representing a group that protects the carboxylic acid functional group may be chosen from the groups described in *Protective Groups in organic synthesis* (T. W. Greene et al., 2$^{nd}$ Edition, Wiley Interscience) such as, for example, a $C_1$-$C_4$ alkyl radical or a cyclic radical (such as a phenyl group).

Among the $C_1$-$C_4$ alkyl radicals, mention may especially be made of methyl, ethyl, isopropyl or tert-butyl radicals, the tert-butyl group being particularly preferred.

Particular compounds conforming to the invention correspond to the formulae (II), (III), (IV), (V), (VI) and (VII) below:

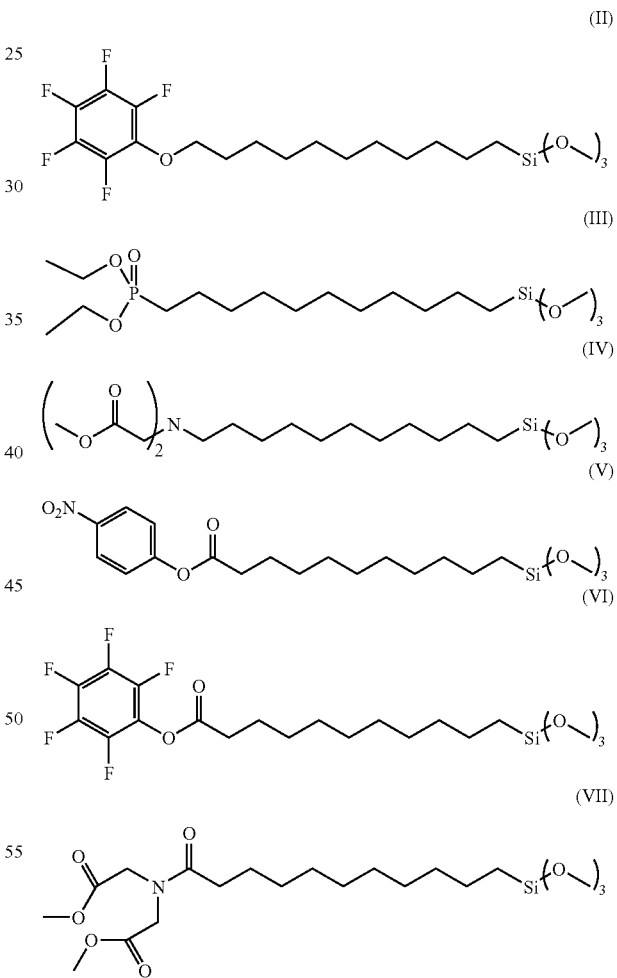

The compounds of the invention may be prepared by conventional synthesis methods that are accessible to a technician specialized in organic synthesis.

By way of example, in order to obtain compounds bearing, at one of their ends, an (a), (c) or (d) group and, at the other end, a X group of the trialkoxysilane type, the preparation may be envisaged in two steps, starting from a precursor compound bearing, at one of its ends, a halogen atom and, at the other end, a vinyl group, according to the following reaction scheme:

1) Formation of the A group from the precursor compound

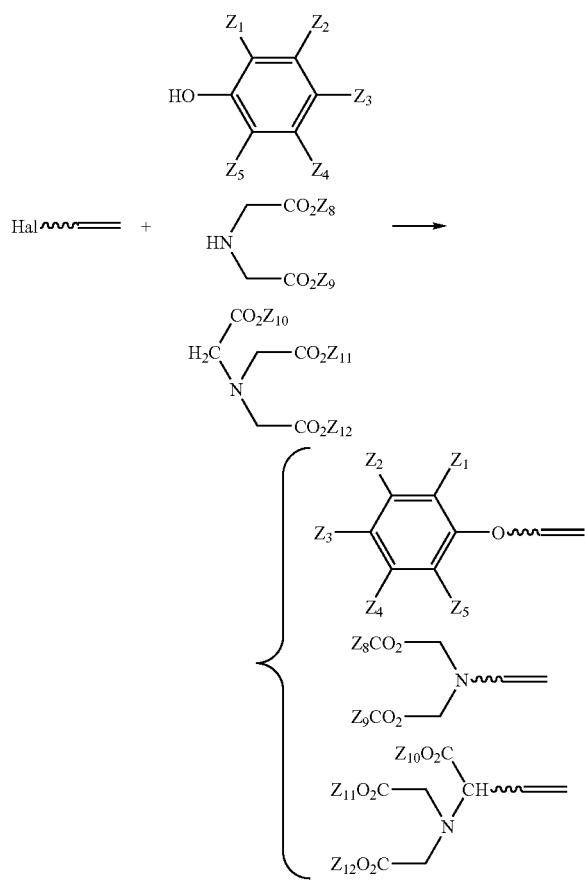

This reaction consists of a nucleophilic substitution of the halogen atom Hal.

2) The compounds obtained at the end of step 1 are then subjected to a hydrosilylation reaction with a reactant of the $HSi(OR)_3$ type in the presence of a Karstedt catalyst $Pt[Si(CH_3)_2HC=CH_2]_2O$.

To obtain the E (e) group, it is sufficient to replace the precursor compound mentioned above with a compound comprising, at one of its ends, a group —COHal instead of a group -Hal and to react with this compound a reactant of formula HO—$Z_{13}$, the second step being identical to that mentioned above.

A person skilled in the art will adapt these reaction schemes as function of the silane compounds that it is desired to obtain.

As mentioned previously, the silane compounds of the invention are capable of being grafted to the surface of a support, due to the presence of the X group that is capable of reacting with the hydroxyl or hydride functional groups (present on the support) in order to form covalent bonds.

Thus, the invention relates, according to a second subject matter, to a process of functionalizing a solid support comprising hydroxyl or hydride functional groups at the surface, comprising a step of bringing a solution comprising at least one silane compound into contact with said support, said silane compound corresponding to one of the following formulae:

A-E-X      (I)

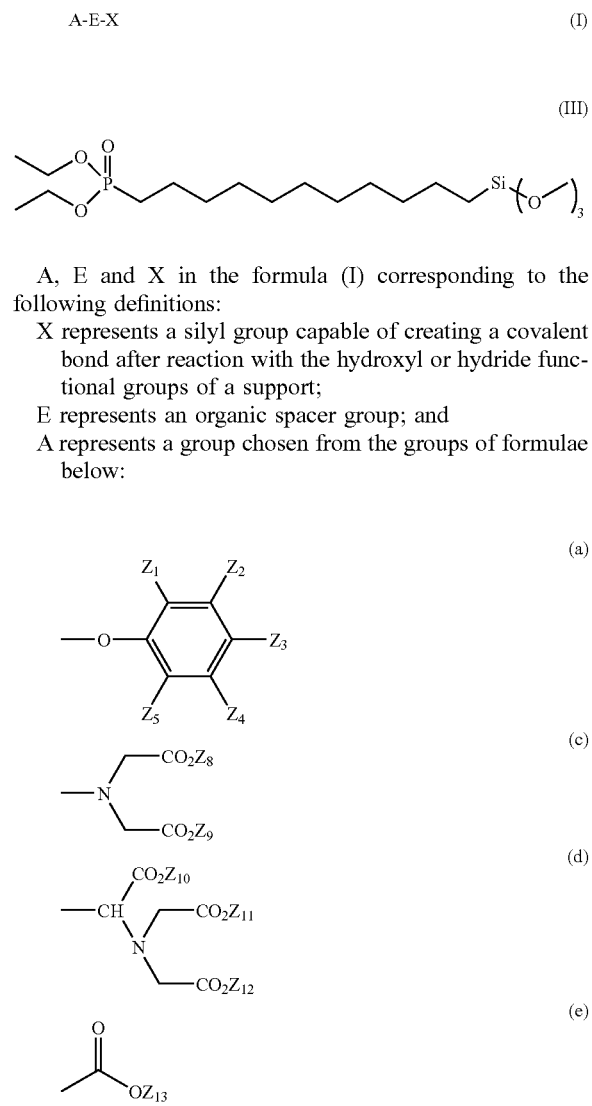

A, E and X in the formula (I) corresponding to the following definitions:

X represents a silyl group capable of creating a covalent bond after reaction with the hydroxyl or hydride functional groups of a support;

E represents an organic spacer group; and

A represents a group chosen from the groups of formulae below:

in which:

$Z_1$ to $Z_5$ independently represent a hydrogen atom or a halogen atom;

$Z_8$ to $Z_{12}$ independently represent a group for protecting the carboxylic acid functional group, a hydrogen atom or a monovalent cation; and $Z_{13}$ represents an imidazole, N-hydroxysuccinimide, nitrophenyl, pentafluorophenyl or acid anhydride group, with the exclusion of phenyloxyundecyltrimethoxysilane.

Compounds (II) to (VII) are particularly suitable for carrying out this process.

X and E may be as defined previously in the section relating to the silane compounds.

This process may first comprise a step of treating the surface of the support in order to create on said surface the hydroxyl or hydride functional groups necessary for the grafting.

Thus, for a support made of silicon (100) (for example of wafer type), it is preferable, before functionalization, to treat the latter by bringing it into contact with a solution of sodium hydroxide in order to generate a hydroxylation reaction.

The supports possibly being functionalized according to the process of the invention may be organic supports (for example made of plastics), inorganic supports, for example supports made of a metal oxide (for example, silica and derivatives thereof such as glass, quartz, indium tin oxide, etc.), metallic supports (such as titanium supports) or supports made of silicon, the main thing being that these supports are capable (optionally with the prior treatment step mentioned above) of having hydroxyl or hydride functional groups for grafting the silane compounds of the invention.

Another subject of the invention is the functionalized solid support capable of being obtained by the process of the invention.

Due to the nature of the A group, the grafted silane compounds have the ability to interact with biological molecules in order to immobilize them.

Therefore, another subject of the present invention is a process of immobilizing biological molecules on a functionalized solid support comprising the following steps:

a) a step of implementing a process of functionalizing a solid support having hydroxyl or hydride functional groups at the surface, comprising a step of bringing a solution comprising at least one silane compound into contact with said support, said silane compound corresponding to one of the following formulae:

A-E-X  (I)

in which:
X represents a silyl group capable of creating a covalent bond after reaction with the hydroxyl or hydride functional groups of a support;
E represents an organic spacer group;
A represents a group chosen from the groups of formulae below:

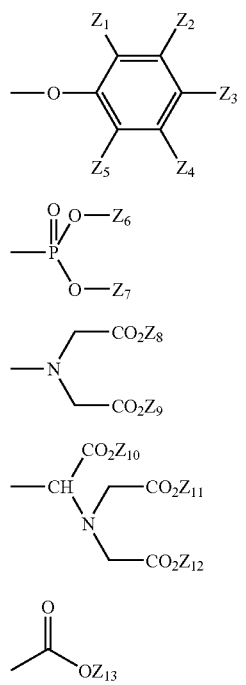

in which:
$Z_1$ to $Z_5$ independently represent a hydrogen atom or a halogen atom;
$Z_6$ and $Z_7$ represent a group for protecting the phosphonic acid functional group, a hydrogen atom or a monovalent cation;
$Z_8$ to $Z_{12}$ independently represent a group for protecting the carboxylic acid functional group, a hydrogen atom or a monovalent cation; and
$Z_{13}$ represents an imidazole, N-hydroxysuccinimide, nitrophenyl, pentafluorophenyl or acid anhydride group,
with the exclusion of phenyloxyundecyltrimethoxysilane;

b) a step of bringing the support obtained in step a) into contact with a solution comprising the biological molecule(s) to be immobilized.

The $Z_6$ and $Z_7$ groups representing a group that protects the phosphonic acid functional group may be chosen from groups such as, for example, a $C_1$-$C_4$ alkyl radical, an aromatic cyclic radical (such as a phenyl group), a silyl radical (such as a —Si(CH$_3$)$_3$ group) and an amino group.

Among the $C_1$-$C_4$ alkyl radicals, mention may especially be made of methyl and ethyl radicals.

The compounds of formulae (II) to (VII) are particularly suitable for carrying out this process.

X and E may be as defined previously in the section describing the silane compounds.

The molecules to be immobilized may be oligonucleotides, nucleic acids, polypeptides (proteins, enzymes), lipids, carbohydrates or hormones.

Within the meaning of the present invention and in what follows, the term "nucleic acids" is understood to mean both oligonucleotides and DNA or RNA, or else nucleic acids with modified backbone or bases, such as peptide nucleic acids (PNAS) which involve peptide bonds instead of phosphodiester bonds.

Depending on the nature of the biological molecule to be isolated and the nature of the grafted silane compound, the immobilization may be carried out according to various mechanisms, such as immobilization by formation of π-π bonds, by ionic interactions or else by complexation with metal ions.

Thus, with supports functionalized with silane compounds comprising an A group of formula:

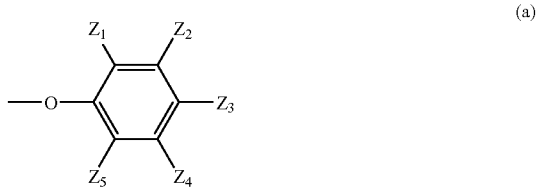

π-π bonds are formed between the aromatic rings of adjacent silane compound molecules at the surface of the functionalized supports, when $Z_1$ to $Z_5$ represent halogen atoms. The biological molecules comprising aromatic rings may easily be trapped by the complexes resulting from the formation of said π-π bonds, such as the biological molecules comprising aromatic amino acids (phenylalanine, tryptophan, tyrosine).

The formation of these π-π bonds is explained by the high electronegativity of the halogen atoms, which generates charge delocalization in the silane compound molecule, thus increasing a donor-acceptor effect and substantially favouring the formation of a π-π bond between two adjacent molecules.

With supports functionalized with silane compounds comprising an A group of formula:

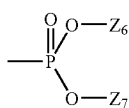
(b)

the immobilization is carried out by ionic interaction, subject to releasing the phosphonic acid functional group (for example, by treatment with iodotrimethylsilane), which functional group will in turn react with an aqueous sodium hydroxide solution to give the phosphonate functional group, which phosphonate functional group is capable of creating ionic interactions with charged biological molecules (for example, proteins), such as is often the case at physiological pH values.

With supports functionalized with silane compounds comprising an A group of formula:

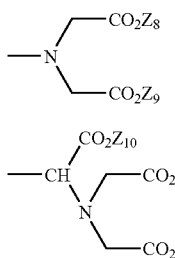
(c)

(d)

the immobilization of the biological molecules may be carried out by complexation, subject to releasing the iminodiacetic acid functional group, for example by acid hydrolysis, then treating the support with a solution containing a metallic element (such as $Ni^{2+}$, $Zn^{2+}$, $Co^{2+}$, $Cu^{2+}$, $Ga^{3+}$) in order to enable the complexation of this element, which element will be able to see its coordination sphere completed by the lone pairs of the biological molecule to be immobilized. This is especially the case for proteins bearing a Histidine-Tag sequence. The histidine functional group is capable of chelating with the free coordination site of a metallic ion itself chelated to an iminodiacetic acid or nitrilodiacetic acid group. The silane compounds according to the invention comprising such groups may therefore be used for the separation and the purification of proteins comprising such a sequence.

For certain silanes (those comprising A groups of formulae (b), (c) and (d)), the process of the invention may comprise, before the contacting step with the molecule to be immobilized, a deprotection step in order to release the phosphonic acid or carboxylic acid functional groups and for those comprising an A group of formula (c) or (d), a subsequent step of complexing with a metallic element, that is to say after the deprotection step.

The silane compounds comprising an A group of formula:

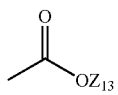
(e)

with $Z_{13}$ representing an imidazole, N-hydroxysuccinimide, nitrophenyl or pentafluorophenyl group, are activated silane ester compounds, insofar as they will allow a direct coupling between their ester functional group and an amine functional group present on a biological molecule. These silane compounds, once grafted to a support, will therefore be able to advantageously be used for immobilizing biological molecules bearing amine functional groups such as proteins or else oligonucleotides.

Another subject of the invention is the solid supports obtained by implementing the immobilization process according to the invention, that is to say the solid supports to which the biological molecules of interest are immobilized by covalent attachment.

These solid supports may thus be used as analysis tools (for example, for a diagnosis, or a sequencing) or as synthesis tools for producing, for example, coatings.

The supports therefore find applications in many fields, such as the synthesis on solid supports, the separation and purification of molecules (electrophoresis and chromatography) and biosensors.

The use of solid supports functionalized according to the present invention makes it possible to immobilize various types of biological molecules and therefore to prepare various types of chips, for instance nucleic acid chips such as DNA chips, and polypeptide chips such as protein chips.

The use of solid supports modified according to the present invention is particularly advantageous for the preparation of DNA chips, namely supports onto which oligonucleotides or polynucleotides of known sequences are attached covalently. Such DNA chips make it possible, via hybridization of the oligonucleotides or polynucleotides immobilized on the support with target oligonucleotides or nucleic acids, to determine the sequence of these target molecules and to follow the expression of the genes.

Therefore, another subject of the present invention is a nucleic acid chip or polypeptide chip, obtained by the aforementioned immobilization process of the invention.

The invention will now be described with reference to the following examples that are given by way of illustration and non-limitingly.

SUMMARY OF PARTICULAR EMBODIMENTS

Example 1

This example illustrates the preparation of a silane compound conforming to the invention: 11-pentafluorophenyl ether undecyltrimethoxysilane according to the following reaction scheme:

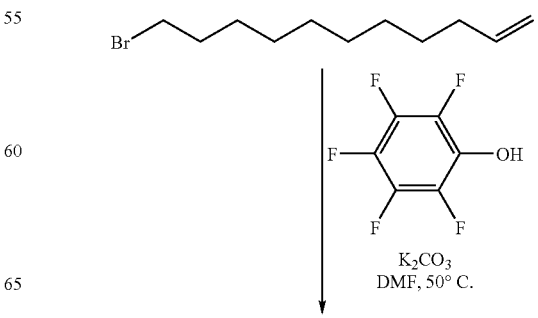

-continued

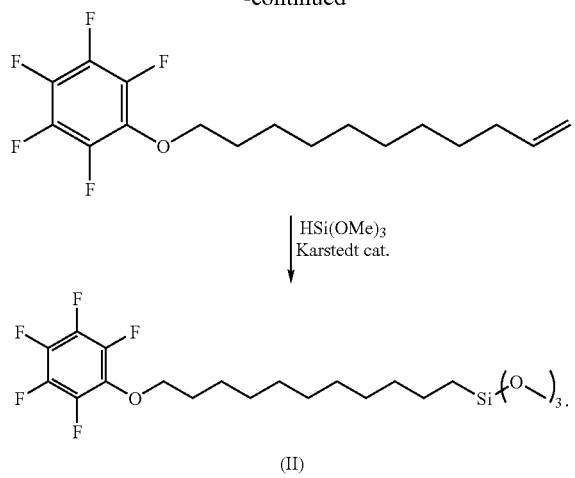

The pentafluorophenyl ether functional group is obtained by reaction of 11-bromoundecene with pentafluorophenol in the presence of potassium carbonate. Next, the incorporation of the silyl group was carried out by a hydrosilylation reaction in the presence of a Karstedt catalyst.

This example also illustrates the silanization of a silicon support by the silane compound (II).

a) Step 1: Synthesis of 11-pentafluorophenyl ether undec-1-ene

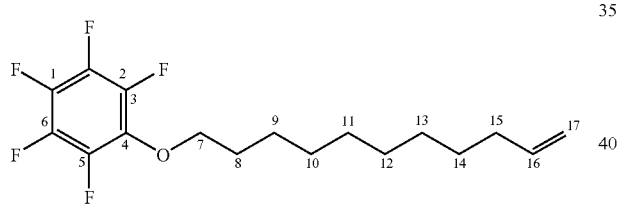

Added to a solution of pentafluorophenol (3.77 g; 21 mmol; 1 eq.) dissolved in 75 ml of DMF, were 11-bromoundecene (95%) (5.02 g; 4.7 ml; 21 mmol) and potassium carbonate (2.83 g; 21 mmol; 1 eq.). The reaction was carried out under reflux for 3 hours. After evaporating the DMF and taking up in dichloromethane, the reaction mixture was successively washed with distilled water (two times) and with a saturated sodium chloride solution, dried over anhydrous magnesium sulphate then concentrated to give a colourless liquid.

The characteristics of the product obtained were the following:

Mass obtained: 5.79 g

Yield: 84%

$^1$H NMR (200 MHz; CDCl$_3$): 1.35 (12H; m; H$^{9-14}$); 1.79 (2H; m; H$^8$); 2.08 (2H; m; H$^{15}$); 4.19 (2H; t; H$^7$; $^3J_{H-H}$=6.5 Hz); 5 (2H; m; H$^{17}$); 5.86 (1H; m; H$^{16}$)

$^{13}$C NMR (200 MHz; CDCl$_3$): 25.16; 29.23; 29.28; 29.42; 29.49; 29.63; 33.72; 34.18; 76.16 (t; C$^7$; $^3J_{C-C}$=3.4 Hz); 114.55 (C$^{17}$); 134.46 (C$^4$); 138.22 (2c; C$^{3+5}$; $^3J_{C-F}$=259 Hz); 139.51 (C$^{16}$); 139.75 (C$^1$); 142.38 (2c; C$^{2+6}$; $^3J_{C-F}$=243 Hz).

b) Step 2: Synthesis of 11-pentafluorophenyl ether undecyltrimethoxysilane (II)

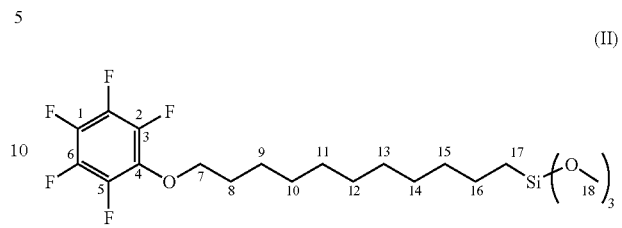

The pentafluorophenyl ether undec-1-ene (5.79 g; 17 mmol) was mixed with trimethoxysilane (90%) (3 g; 3.1 ml; 22 mmol; 1.3 eq.). The Karstedt catalyst (0.04 g; 0.04 mmol; 0.0025 eq.) was added very slowly. The reaction took place at ambient temperature over 12 hours. The crude reaction product was purified by distillation to give a colourless liquid.

The characteristics of the product obtained were the following:

Mass obtained: 5.69 g

Boiling point: 130-135° C. at 0.5 mbar

Yield: 72%

$^1$H NMR (200 MHz; CDCl$_3$): 0.64 (2H; m; H$^{17}$); 1.27 (16H; m; H$^{9-16}$); 1.75 (2H; m; H$^8$); 3.56 (9H; s; H$^{18}$); 4.13 (2H; t; H$^7$; $^3J_{H-H}$=6.5 Hz)

$^{13}$C NMR (200 MHz; CDCl$_3$): 9.45 (C$^{17}$); 22.94; 25.85; 29.57; 29.6; 29.83 (2C); 29.89; 30.17; 33.48; 50.67 (3C; C$^{18}$); 76.16 (t; C$^7$; $^3J_{C-C}$=3.4 Hz); 134.46 (C$^4$); 138.22 (2C; C$^{3+5}$; $^3J_{C-F}$=259 Hz); 139.51 (C$^{16}$); 142.38 (2C; C$^{2+6}$; $^3J_{C-F}$=243 Hz)

Si NMR (200 MHz; CDCl$_3$): −41.29 (s)

c) Silanization of a Silicon Support by Compound (II)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

The grafted support had the following configuration:

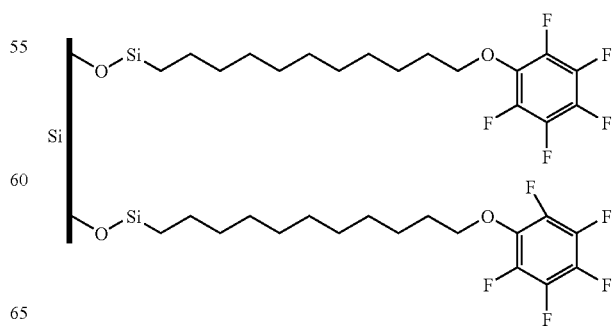

Example 2

This example illustrates the preparation of a silane compound conforming to the invention: 11-(diethylphosphonate)undecyltrimethoxysilane (III) according to the following reaction scheme:

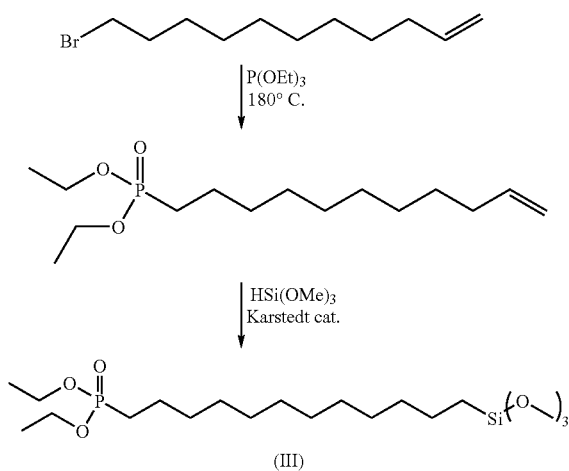

The phosphonic acid functional group was protected in the diethylphosphonate form after reaction of 11-bromoundecene with triethylphosphate at high temperature.

Next, the incorporation of the silyl group was carried out by a hydrosilylation reaction in the presence of a Karstedt catalyst.

This example also illustrates the silanization of a silicon support by the silane compound (III).

a) Step 1: Synthesis of 11-(diethylphosphonate)undec-1-ene

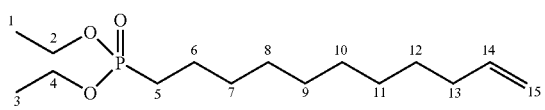 [SMILES: C=CCCCCCCCCCP(=O)(OCC)OCC]

11-Bromoundecene (95%) (12.64 g; 11.8 ml; 52 mmol) was mixed with triethylphosphate (98%) (17.24 g; 17.8 ml; 102 mmol; 2 eq.). The solution was heated at 170° C. for 24 hours, then the crude reaction product was purified by distillation to give a colourless liquid.

The characteristics of the product obtained were the following:

Mass obtained: 13.55 g

Boiling point: 115-120° C. at 0.5 mbar

Yield: 91%

$^1$H NMR (200 MHz; CDCl$_3$): 1.29 (12H; m; H$^{7-12}$); 1.32 (6H; t; H$^{1+3}$; $^3J_{H-H}$=7.1 Hz); 1.51-1.94 (4H; m; H$^{5+6}$); 2.04 (2H; m; H$^{13}$); 4.09 (4H; m; H$^{2+4}$); 4.97 (2H; m; H$^{15}$); 5.81 (1H; m; H$^{14}$)

$^{13}$C NMR (200 MHz; CDCl$_3$): 16.75 (2C; d; C$^{1+3}$; $^3J_{C-P}$=6.2 Hz); 21.25; 22.69 (d; C$^7$; $^3J_{C-P}$=5.4 Hz); 24.58-27.37 (d; C$^5$; $^1J_{C-P}$=140.3 Hz); 29.20; 29.37; 29.60; 29.69; 30.88 (d; C$^6$; $^2J_{C-P}$=16.9 Hz); 34.09; 61.60 (2C; d; C$^{2+4}$; $^2J_{C-P}$=5.9 Hz); 114.43 (C$^{15}$); 139.35 (C$^{14}$).

b) Step 2: Synthesis of 11-(diethylphosphate)undecyltrimethoxysilane (III)

11-(Diethylphosphonate)undec-1-ene (4.99 g; 17 mmol) was mixed with trimethoxysilane (90%) (3.3 g; 3.3 ml; 23 mmol; 1.3 eq.). The Karstedt catalyst (0.04 g; 0.04 mmol; 0.0025 eq.) was added very slowly. The reaction took place at ambient temperature over 16 hours. The crude reaction product was purified by distillation to give a colourless liquid.

The characteristics of the product obtained were the following:

Mass obtained: 4.22 g

Boiling point: 165-170° C. at 0.5 mbar

Yield: 60%

$^1$H NMR (200 MHz; CDCl$_3$): 0.65 (2H; m; H$^{15}$); 1.26 (16H; m; H$^{7-14}$); 1.32 (6H; t; H$^{1+3}$; $^3J_{H-H}$=7 Hz); 1.53-1.81 (4H; m; H$^{5+6}$); 3.56 (9H; s; H$^{16}$); 4.09 (4H; m; H$^{2+4}$)

$^{13}$C NMR (200 MHz; CDCl$_3$): 9.52 (C$^{15}$); 16.87 (2C; d; C$^{1+3}$; $^3J_{C-P}$=6.1 Hz); 22.74; 22.91 (d; C$^7$; $^3J_{C-P}$=6.1 Hz); 24.69-27.47 (d; C$^5$; $^1J_{C-P}$=140.3 Hz); 29.48; 29.63; 29.76; 29.86; 29.97; 31.01 (d; C$^6$; $^2J_{C-P}$=17 Hz); 33.53; 50.87 (3C; C$^{16}$); 61.74 (2C; d; C$^{2+4}$; $^2J_{C-P}$=6.2 Hz).

c) Silanization of a Silicon Support by the Compound (III)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

The grafted support had the following configuration:

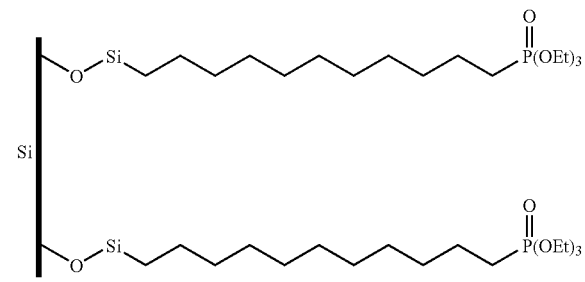

The grafted support was then brought into contact with a solution of iodotrimethylsilane in order to release the phosphonic acid functional group, which will in turn react with an aqueous sodium hydroxide solution to give the desired phosphonate functional group according to the following reaction scheme:

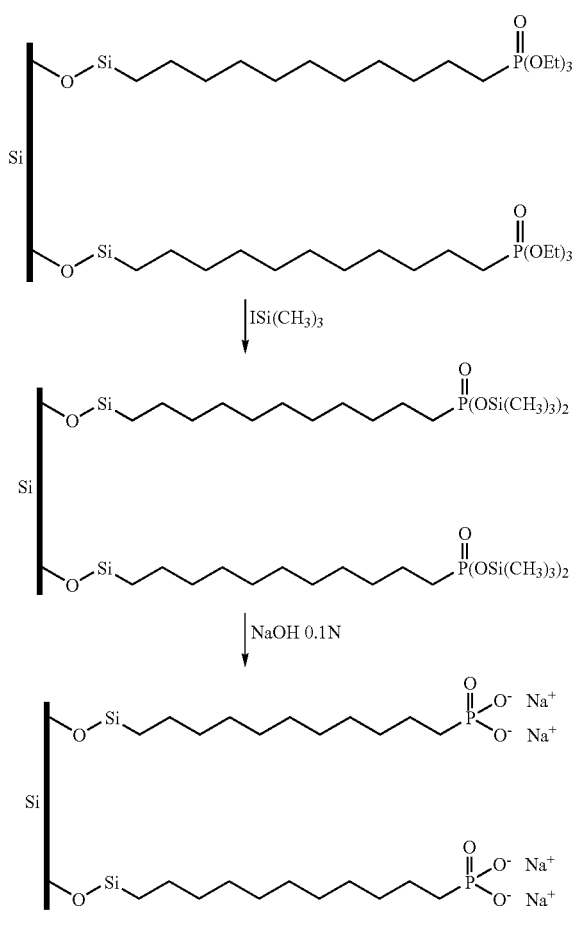

The support thus charged may be used to adsorb, in a specific manner, charged proteins (such as protein markers) via ionic interaction.

Example 3

This example illustrates the preparation of a silane compound conforming to the invention: trimethoxysilanylundecyl-10-iminodiacetic acid methyl ester (IV) according to the following reaction scheme:

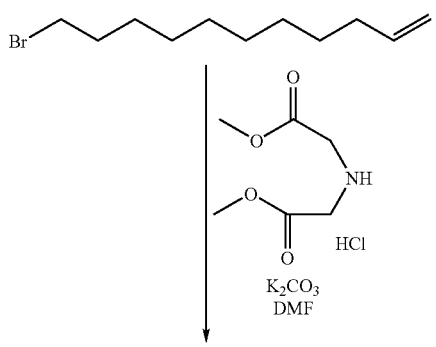

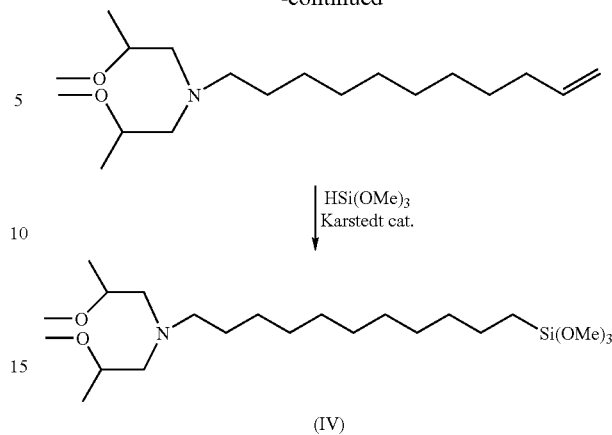

(IV)

The amine functional group is incorporated via a Williamson type reaction between the dimethyliminodiacetate and the 11-bromoundecene in the presence of potassium carbonate.

Next, the incorporation of the silyl group was carried out by a hydrosilylation reaction in the presence of a Karstedt catalyst.

This example also illustrates the silanization of a silicon support by the silane compound (IV).

a) Step 1: Synthesis of undec-1-eneiminodiacetic acid methyl ester

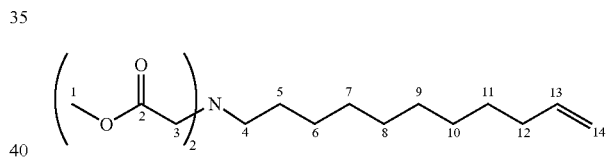

Added to a solution of dimethyliminodiacetate (hydrochloride) (8.53 g; 43 mmol; 1 eq.) dissolved in 250 ml of DMF, were triethylamine (4.35 g; 6 ml; 43 mmol; 1 eq.), 11-bromoundecene (95%) (10.53 g; 9.9 ml; 43 mmol) and potassium carbonate (5.95 g; 43 mmol; 1 eq.). The reaction was heated at 80° C. over 36 hours. After evaporating the DMF and taking up in ethyl acetate, the reaction mixture was washed successively with distilled water (two times) and with a saturated sodium chloride solution and dried over anhydrous magnesium sulphate. The residue was purified by chromatography over silica gel (cyclohexane/ethyl acetate (75/25)) to give a colourless liquid.

The characteristics of the product obtained were the following:

Mass obtained: 6 g

Yield: 84%

$^1$H NMR (200 MHz; CDCl$_3$): 1.28 (12H; m; H$^{6-12}$); 1.59 (2H; m; H$^5$); 2.03 (2H; m; H$^{12}$); 3.74 (6H; s; H1); 4.09 (4H; t; H$^{3+4}$; $^3J_{H-H}$=6.8 Hz); 4.16 (2H; s; H$^3$); 4.97 (2H; m; H$^{14}$); 5.81 (1H; m; H$^{16}$)

$^{13}$C NMR (200 MHz; CDCl$_3$): 26.14; 29.20; 29.29; 29.48; 29.59; 29.77; 29.84; 34.18; 49.51 (C$^3$); 52.54 (C$^1$); 66.89 (C$^4$); 114.52 (C$^{14}$); 139.57 (C$^{13}$); 170.40 (C$^2$).

b) Step 2: Synthesis of trimethoxysilanylundecyl-10-iminodiacetic acid methyl ester

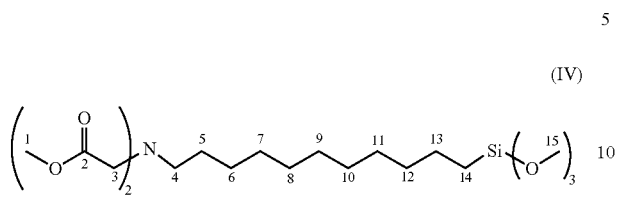

(IV)

Undec-1-eneiminodiacetic acid methyl ester (6 g; 19 mmol) was mixed with trimethoxysilane (90%) (3.57 g; 3.7 ml; 26 mmol; 1.4 eq.). The Karstedt catalyst (0.05 g; 0.05 mmol; 0.0025 eq.) was added very slowly. The reaction took place at ambient temperature over 16 hours. The crude reaction product was purified by distillation to give a colourless liquid.

The characteristics of the product obtained were the following:

Mass obtained: 3.83 g
Boiling point: 185-190° C. at 0.5 mbar
Yield: 46%

$^1$H NMR (200 MHz; CDCl$_3$): 0.65 (2H; m; H$^{14}$); 1.26 (16H; m; H$^{6-13}$); 1.60 (2H; m; H$^5$); 3.57 (9H; s; H$^{15}$); 3.74 (6H; s; H$^1$); 4.09 (4H; t; H$^{3+4}$; $^3$J$_{H-H}$=6.8 Hz); 4.16 (2H; s; H$^3$)

$^{13}$C NMR (200 MHz; CDCl$_3$): 9.42 (C$^{14}$); 22.95; 26.12; 29.18; 29.54; 29.61; 29.88 (2C)$^2$; 29.92; 33.49; 49.49 (C$^3$); 50.83 (3C; C$^{15}$); 52.50 (C$^1$); 66.86 (C$^4$); 170.29 (C$^2$);

Si NMR (200 MHz; CDCl$_3$): −41.27 (s)

c) Silanization of a Silicon Support by the Compound (IV)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

The grafted support had the following configuration:

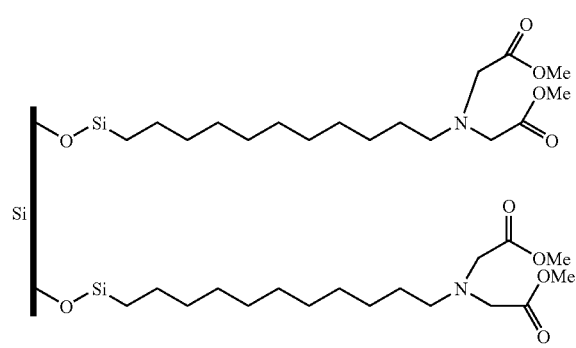

The iminodiacetic acid functional group was then released by reaction of the modified support with 12N HCl, then the thus treated support was reacted with an aqueous copper sulphate solution to enable the copper complexation according to the following reaction scheme:

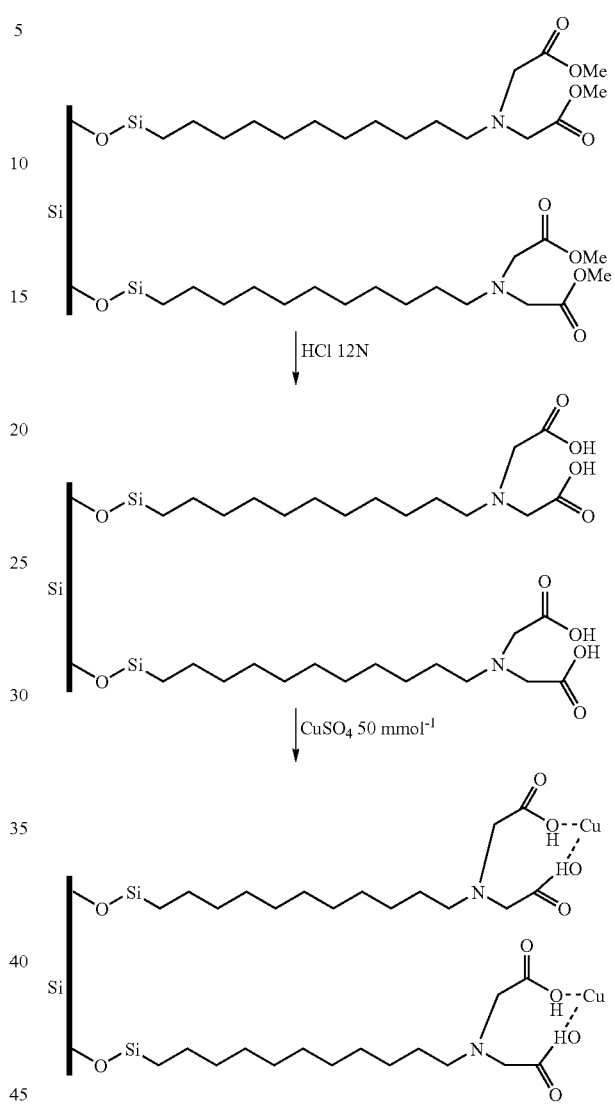

Such a complex may advantageously be used to ensure the retention of a protein comprising a sequence known as "Histidine-Tag". Histidine-Tag is a sequence corresponding to a consecutive linking of 5 to 6 histidines placed in the terminal C or N position of a protein and comprising an imidazole functional group in its side chain. This functional group is capable of chelating with the free coordination site of a metallic ion that is itself chelated to an iminodiacetic acid or nitrilodiacetic acid group (in this case the metallic ion is Cu$^{2+}$). Metallic ions that can also be envisaged may be Ni$^{2+}$, Zn$^{2+}$ or Co$^{2+}$.

The grafted silane compounds described above may therefore be used for the separation and purification of proteins bearing the Histidine-Tag sequence.

Example 4

This example illustrates the preparation of a silane compound conforming to the invention: 4-nitrophenylundecylt-rimethoxysilane ester (V) according to the following reaction scheme:

The ester functional group is synthesized by reaction between undecenoyl chloride and 4-nitrophenol.

Next, the incorporation of the silyl group is carried out by a hydrosilylation reaction in the presence of a Karstedt catalyst.

a) Step 1: Synthesis of 4-nitrophenylundec-1-ene ester

Added to a solution of 4-nitrophenol (3.25 g; 23 mmol; 1 eq.) dissolved in 50 ml of anhydrous ether, was pyridine (1.85 g; 1.9 ml; 23 mmol; 1 eq.). The solution was heated under reflux of ether and undecenoyl chloride (97%) (4.9 g; 5.2 ml; 23 mmol; 1 eq.) was added very slowly (over a period of around 1 hour). The reaction was continued under reflux of ether for 1 hour. The reaction mixture was filtered, then the filtrate was concentrated to give a yellowish liquid.

The characteristics of the product obtained were the following:

Mass obtained: 7.1 g

Yield: 100%

$^1$H NMR (200 MHz; CDCl$_3$): 1.33 (10H; m; H$^{10-14}$); 1.74 (2H; m; H$^9$); 2.04 (2H; m; H$^{15}$); 2.60 (2H; t; H$^8$; $^3J_{H-H}$=7.5 Hz); 4.98 (2H; m; H$^{17}$); 5.80 (1H; m; H$^{16}$); 7.27 (2H; d; H$^{3+5}$; $^3J_{H-H}$=9.2 Hz); 8.27 (2H; d; H$^{2+6}$; $^3J_{H-H}$=9.2 Hz)

$^{13}$C NMR (200 MHz; CDCl$_3$): 25.13; 29.28; 29.43 (2C); 29.56; 29.66; 34.17; 34.73; 114.61 (C$^{17}$); 122.84 (2C; C$^{3+5}$); 125.59 (2C; C$^{2+6}$); 139.52 (C$^{16}$); 145.66 (C$^1$) 155.96 (C$^4$); 171.73 (C$^7$).

b) Step 2: Synthesis of 4-nitrophenylundecyltrimethoxysilane ester (V)

4-Nitrophenylundec-1-ene ester (7.54 g; 25 mmol) was mixed with trimethoxysilane (90%) (4.25 g; 4.5 ml; 31 mmol; 1.3 eq.). The Karstedt catalyst (0.06 g; 0.06 mmol; 0.0025 eq.) was added very slowly and the whole mixture was heated at 140° C. under argon over 24 hours. The crude reaction product was purified by distillation to give a yellowish liquid.

The characteristics of the product obtained were the following:

Mass obtained: 5.02 g

Boiling point: 170-175° C. at 0.5 mbar

Yield: 48%

$^1$H NMR (200 MHz; CDCl$_3$): 0.65 (2H; m; H$^{17}$); 1.33 (10H; m; H$^{10-16}$); 1.74 (2H; m; H$^9$); 2.60 (2H; t; H$^8$; $^3J_{H-H}$=7.5 Hz); 3.57 (9H; s; H$^{18}$); 7.28 (2H; d; H$^{3+5}$; $^3J_{H-H}$=9.2 Hz); 8.25 (2H; d; H$^{2+6}$; $^3J_{H-H}$=9.2 Hz)

$^{13}$C NMR (200 MHz; CDCl$_3$) 9.48 (C$^{17}$); 22.95; 25.07; 29.39; 29.57 (2C); 29.78 (2C); 33.46; 34.59; 50.78 (3C; C$^{18}$); 122.82 (2C; C$^{3+5}$); 125.47 (2C; C$^{2+6}$); 145.53 (C$^1$) 155.91 (C$^4$) 171.62 (C$^7$)

Si NMR (200 MHz; CDCl$_3$): −41.22 (s)

c) Silanization of a Silicon Support by the Compound (V)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

d) Immobilization of an Oligonucleotide onto the Grafted Support

Hybridization and Analysis

Deposits of a solution of oligonucleotides having the following sequence:

5' TTT TTGATA AAC CCC 3' modified at 5' by an amine functional group and deposits of a solution of oligonucleotides having the following sequence:

5' TTT TTGATA AAC CCC 3' that were unmodified were carried out on the support obtained in accordance with what was described in paragraph c), these deposits being carried out manually in an amount of 0.2 μl. The oligonucleotide concentration of the solutions used was 10 μM in a 0.1M NaCl buffer.

After an incubation time of 16 hours in a humid chamber, the supports were hybridized with a solution of complementary targets having the following sequence:

```
5' CAT AGA GTG GGT TTA TCC A 3'
``` having a concentration of 0.05 μM, labelled with a fluorescent Cy3 group.

The fluorescence signals were measured on a scanner sold under the name GenePix by Axon.

The results show that the supports grafted in accordance with the invention make it possible to achieve the immobilization of oligonucleotides comprising an amine functional group and of unmodified oligonucleotides, that is to say those bearing a free —OH functional group.

Example 5

This example illustrates the preparation of a silane compound conforming to the invention: pentafluorophenylundecyltrimethoxysilane ester (VI) according to the following reaction scheme:

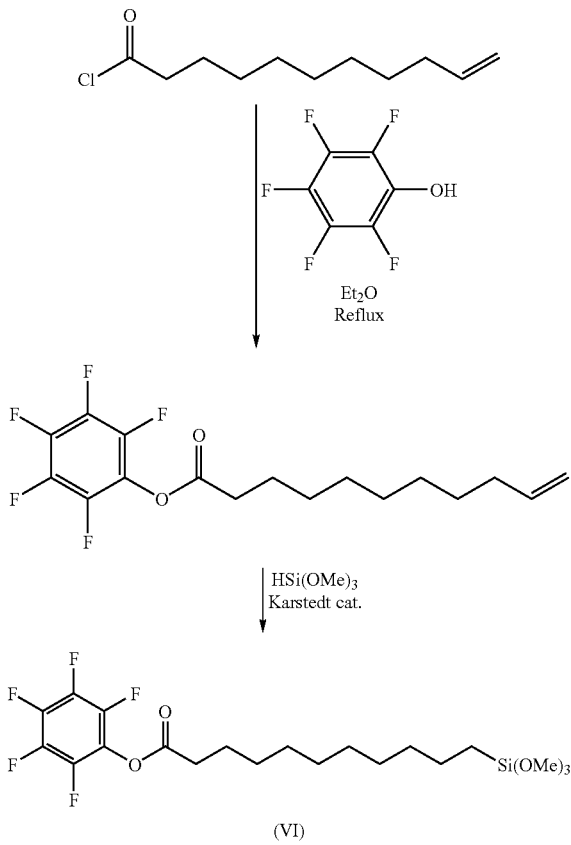

The ester functional group was synthesized by reaction between undecenoyl chloride and pentafluorophenol.

Next, the incorporation of the silyl group was carried out by a hydrosilylation reaction in the presence of a Karstedt catalyst.

a) Step 1: Synthesis of pentafluorophenylundec-1-ene ester

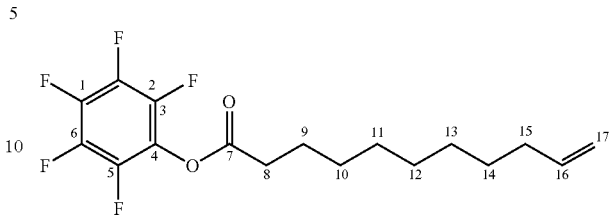

Added to a solution of pentafluorophenol (6.51 g; 35 mmol, 1 eq.) dissolved in 60 ml of anhydrous ether was pyridine (2.8 g; 2.9 ml; 35 mmol; 1 eq.). The solution was heated under reflux of ether and undecenoyl chloride (97%) (7.4 g; 7.8 ml; 35 mmol; 1 eq.) was added very slowly (over a period of around 1 hour). The reaction was continued under reflux of ether for 1 hour. The reaction mixture was filtered, then the filtrate was concentrated to give a colourless liquid.

The characteristics of the product obtained were the following:

Mass obtained: 12.36 g
Yield: 100%
$^1$H NMR (200 MHz; CDCl$_3$): 1.37 (10H; m; H$^{10-14}$); 1.80 (2H; m; H$^9$); 2.09 (2H; m; H$^{15}$); 2.70 (2H; t; H$^8$; $^3J_{H-H}$=7.4 Hz) 5.01 (2H; m; H$^{17}$); 5.85 (1H; m; H$^{16}$)
$^{13}$C NMR (200 MHz; CDCl$_3$): 25.16; 29.23; 29.28; 29.42; 29.49; 29.63; 33.72; 34.18; 114.55 (C$^{17}$); 135.78-140.77 (2C; m; C$^{3+5}$; $^1J_{C+F}$=251 Hz); 137.29-142.31 (2C; m; C$^{2+6}$; $^1J_{C-F}$=253 Hz); 138.99 (C$^4$); 139.51 (C$^{16}$); 144.07 (C$^1$); 169.97 (C$^7$)
F NMR (400 MHz; CDCl$_3$): −153.38 (2F; d; F$^{3+4}$; $^3J_{F-F}$=17.1 Hz); −158.82 (t; F$^1$; $^3J_{F-F}$=21.6 Hz; −163.02 (2F; t; F$^{2+5}$; $^3J_{F-F}$=16.8 Hz)

b) Step 2: Synthesis of the pentafluorophenylundecyltrimethoxysilane ester (VI)

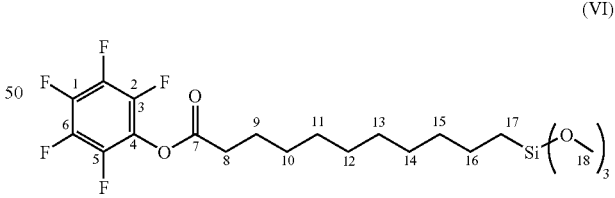

The pentafluorophenylundec-1-ene ester (10.86 g; 31 mmol) was mixed with trimethoxysilane (90%) (5.65 g; 5.9 ml; 42 mmol; 1.4 eq.). The Karstedt catalyst (0.07 g; 0.08 mmol; 0.0025 eq.) was added very slowly. The reaction took place at ambient temperature over 16 hours. The crude reaction product was purified by distillation to give a colourless liquid.

The characteristics of the product obtained were the following:

Mass obtained: 10.69 g
Boiling point: 135-140° C. at 0.5 mbar
Yield: 73%

$^1$H NMR (200 MHz; CDCl$_3$): 0.68 (2H; m; H$^{17}$); 1.32 (14H; m; H$^{10-16}$); 1.80 (2H; m; H$^9$); 2.69 (2H; t; H$^8$; $^3$J$_{H-H}$=7.4 Hz); 3.60 (9H; m; H$^{18}$)

$^{13}$C NMR (200 MHz; CDCl$_3$): 9.52 (C$^{17}$); 22.99; 25.16; 29.25; 29.51; 29.60; 29.78 (2C); 33.51; 33.75; 50.84 (3C; C$^{18}$); 135.73-140.76 (2C; m; C$^{3+5}$; $^1$J$_{C-F}$=253 Hz); 137.27-142.25 (2C; m; C$^{2+6}$; $^1$J$_{C-F}$=251 Hz); 138.98 (C$^4$); 144.06 (C$^1$); 169.95 (C$^7$)

F NMR (400 MHz; CDCl$_3$): −153.31 (2F; d; F$^{3+4}$; $^3$J$_{F-F}$=17.4 Hz=; −158.76 (t; F$^1$; $^3$J$_{F-F}$=21.7 Hz); −162.98 (2F; t; F$^{2+5}$; $^3$J$_{F-F}$=16.4 Hz)

Si NMR (200 MHz; CDCl$_3$): −41.22 (s)

c) Silanization of a Silicon Support by the Compound (VI)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

d) Immobilization of an Oligonucleotide onto the Grafted Support

Hybridization and Analysis

Deposits of a solution of oligonucleotides having the following sequence:

5' TTT TTGATA AAC CCC 3' modified at 5' by an amine functional group and deposits of a solution of oligonucleotides having the following sequence:
5' TTT TTGATA AAC CCC 3'
that were unmodified were carried out on the support obtained in accordance with what was described in paragraph c), these deposits being carried out either manually in an amount of 0.2 μl, or using a piezoelectric ejection robot sold under the name BCA1 by Perkin Elmer, in an amount of 300 pl. The oligonucleotide concentration of the solutions used was 10 μM in a 0.1M NaCl buffer or a 0.3M Na$_2$HPO$_4$ buffer+6% glycerol+4% butanol.

After an incubation time of 16 hours in a humid chamber or in a dry chamber, the supports were hybridized with a solution of complementary targets having the following sequence:

5' CAT AGA GTG GGT TTA TCC A 3' having a concentration of 0.05 μM, labelled with a fluorescent Cy3 group.

The fluorescence signals were measured on a scanner sold under the name GenePix by Axon.

The results show that the supports grafted in accordance with the invention make it possible to achieve the immobilization of oligonucleotides comprising an amine functional group and of unmodified oligonucleotides, that is to say those bearing a free —OH functional group.

e) Immobilization of Streptavidine Cy3

On a support obtained in accordance with what was described in paragraph c), deposits of a streptavidine solution were carried out manually in an amount of 0.2 μl. The protein concentration of the solutions used was 0.001 mg/ml in a 0.01M PBS buffer (phosphate buffered saline).

After an incubation time of 16 hours in a humid chamber, the supports were analysed with a scanner sold under the name GenePix by Axon.

The results show that the modified supports make it possible to achieve the immobilization of this protein.

Example 6

This example illustrates the preparation of a silane compound conforming to the invention: 1-trimethoxysilanyl-10-amidoundecyl-11-iminodiacetic acid methyl ester of formula (VII) according to the following reaction scheme:

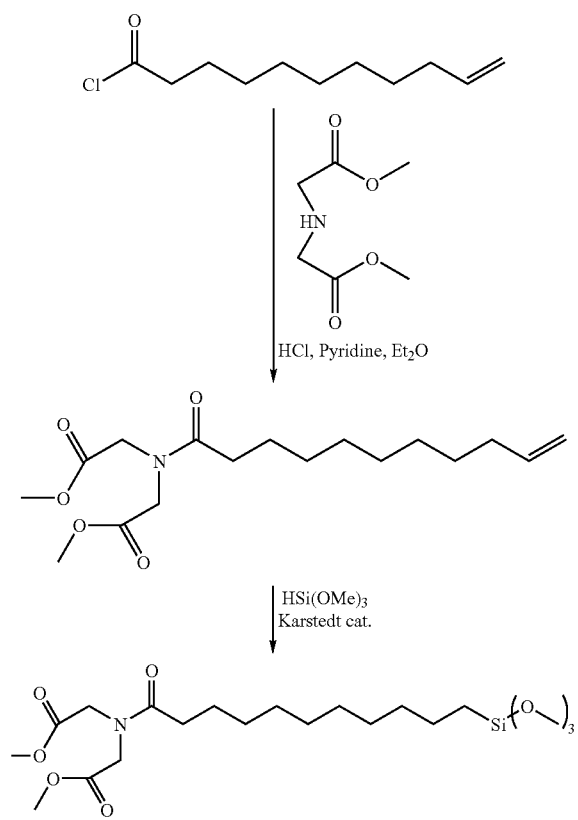

The amide functional group is synthesized by reaction between undecenoyl chloride and dimethyliminodiacetate. The incorporation of the silyl group is carried out by a hydrosilylation reaction.

a) Step 1: Synthesis of 10-amidoundec-1-eneiminodiacetic acid methyl ester

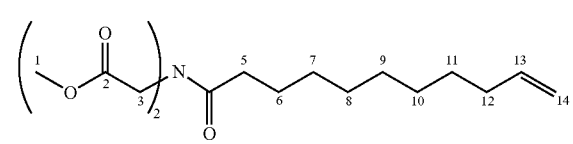

Added to a solution of dimethyliminodiacetate (hydrochloride) (3.08 g; 16 mmol) dissolved in 50 ml of anhydrous ether was pyridine (2.46 g; 2.59 ml; 35 mmol; 2 eq.). The solution was heated under reflux of ether and the undecenoyl chloride (97%) (3.48 g, 3.7 ml, 17 mmol, 1 eq.) was added very slowly (approximately over a period of one hour). The reaction was continued under reflux of ether for 1 hour. The reaction mixture was filtered, then the filtrate was concentrated to give a residue which was then purified by chromatography over silica gel (cyclohexane→cyclohexane/ethyl acetate (70/30)) to give a white solid.

The characteristics of the product obtained were the following:

Mass obtained: 3.85 g
Yield: 74%

$^1$H NMR (200 MHz; CDCl$_3$): 1.30 (10H; m; H$^{7-11}$); 1.64 (2H; m; H$^6$); 2.03 (2H; m; H$^{12}$); 2.30 (2H; t; H$^5$; J$_{H-H}$=7.4 Hz); 3.72 (3H; s; H$^1$); 3.77 (3H; s; H$^1$); 4.16 (2H; s; H$^3$); 4.19 (2H; s; H$^3$); 4.96 (2H; m; H$^{14}$); 5.81 (1H; m; H$^{13}$)

$^{13}$C NMR (200 MHz; CDCl$_3$): 25.18 (C$^6$); 29.28; 29.45; 29.59; 29.69; 29.74; 33.06 (C$^5$); 34.18 (C$^{12}$); 48.18 (C$^3$); 50.34 (C$^3$); 52.53 (C$^1$); 52.90 (C$^1$); 114.52 (C$^{14}$); 139.58 (C$^{13}$); 169.88 (C$^2$); 170.30 (C$^2$); 174.02 (C$^4$)

Melting point: 25-30° C.

b) Step 2: Synthesis of 1-trimethoxysilanyl-10-amidoundecyl-11-iminodiacetic acid methyl ester (VII)

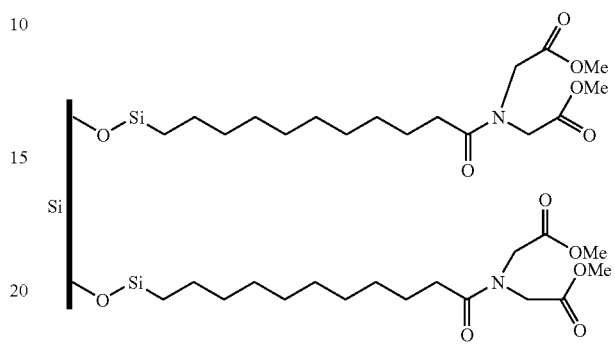

11-amidoundec-1-eneiminodiacetic acid methyl ester (3.34 g; 10 mmol) was mixed with trimethoxysilane (95%) (2.05 g; 2.1 ml; 16 mmol; 1.6 eq.). The Karstedt catalyst (0.024 g; 0.025 mmol; 0.0025 eq.) was added very slowly. The reaction took place at ambient temperature over 16 hours. The crude reaction product was purified by extraction with pentane to give a viscous yellowy liquid.

The characteristics of the product obtained were the following:

Mass obtained: 3 g
Yield: 66%

$^1$H NMR (200 MHz; CDCl$_3$): 0.65 (2H; m; H$^{14}$); 1.26 (14H; m; H$^{7-13}$); 1.61 (2H; m; H$^6$); 2.30 (2H; t; H$^5$; $^3$J$_{H-H}$=7.4 Hz); 3.57 (9H; s; H$^{15}$); 3.73 (3H; s; H$^1$); 3.78 (3H; s; H$^1$); 4.16 (2H; s; H$^3$); 4.19 (2H; s; H$^3$)

$^{13}$C NMR (200 MHz; CDCl$_3$): 9.52 (C$^{14}$); 23.00 (C$^{13}$); 25.23 (C$^6$); 29.65 (2C); 29.82; 29.88; 29.90; 33.12 (C$^5$); 33.56 (C$^{12}$); 48.20 (C$^3$); 50.38 (C$^3$); 50.91 (C$^{15}$); 52.57 (C$^1$); 52.93 (C$^1$); 169.90 (C$^2$); 170.34 (C$^2$); 174.05 (C$^4$)

c) Silanization of a Silicon Support by the Compound (VII)

First, the silicon support, covered with a 5000 Å thick layer of thermal oxide, is subjected to a hydroxylation by bringing into contact with a 3.5M sodium hydroxide solution over two hours.

A solution comprising the silane compound prepared above at a concentration of 10$^{-2}$M in anhydrous trichloroethylene was used, and the silanization reactions were carried out at a controlled temperature of 2° C. over 24 hours.

The grafted support had the following configuration:

The iminodiacetic acid functional group was then released by reaction of the modified support with 10$^{-2}$M AlI$_3$/CH$_3$CN, then the thus treated support was reacted with an aqueous copper sulphate solution in order to enable the copper complexation according to the following reaction scheme:

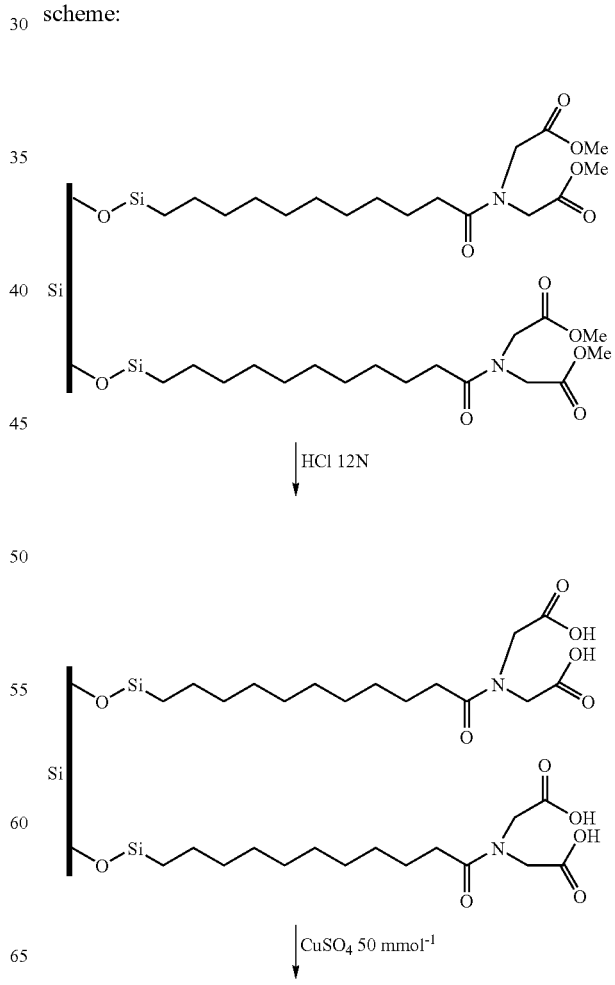

-continued

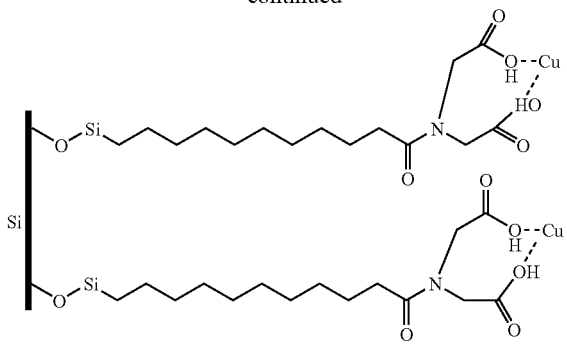

Such a complex may advantageously be used to ensure the retention of a protein comprising a sequence known as "Histidine-Tag". Histidine-Tag is a sequence corresponding to a consecutive linking of 5 to 6 histidines placed in the terminal C or N position of a protein and comprising an imidazole functional group in its side chain. This functional group is capable of chelating with the free coordination site of a metallic ion that is itself chelated to an iminodiacetic acid group (in this case the metallic ion is $Cu^{2+}$). Metallic ions that can also be envisaged may be $Ni^{2+}$, $Zn^{2+}$ or $Co^{2+}$.

The grafted silane compounds described above may therefore be used for the separation and purification of proteins bearing the Histidine-Tag sequence.

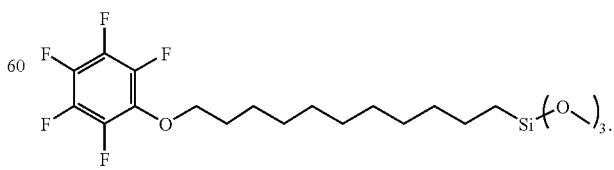

The invention claimed is:

1. A compound of formula (II) below: